United States Patent
Repka et al.

(10) Patent No.: US 6,375,963 B1
(45) Date of Patent: Apr. 23, 2002

(54) BIOADHESIVE HOT-MELT EXTRUDED FILM FOR TOPICAL AND MUCOSAL ADHESION APPLICATIONS AND DRUG DELIVERY AND PROCESS FOR PREPARATION THEREOF

(76) Inventors: Michael A. Repka; Staci L. Repka, both of 700 Oak Hill Dr., Oxford, MS (US) 38655; James W. McGinity, 4209 Dunning La., Austin, TX (US) 78746

(*) Notice: Subject to any disclaimer, the term of this patent is extended or adjusted under 35 U.S.C. 154(b) by 0 days.

(21) Appl. No.: 09/594,294

(22) Filed: Jun. 15, 2000

Related U.S. Application Data (60) Provisional application No. 60/139,411, filed on Jun. 16, 1999.

(51) Int. Cl.[7] .......................... A01N 25/34; A61F 13/00; A61F 9/02; A61L 15/16
(52) U.S. Cl. .................. 424/402; 424/404; 424/447; 424/448; 424/449; 424/434; 424/435; 424/436
(58) Field of Search ................................ 424/402, 404, 424/447, 448, 449, 434, 435, 436

(56) References Cited

U.S. PATENT DOCUMENTS

| | | | |
|---|---|---|---|
| 4,569,837 A | * | 2/1986 | Suzuki et al. ............... 424/28 |
| 4,713,242 A | | 12/1987 | Schiraldi et al. |
| RE33,093 E | | 10/1989 | Schiraldi et al. |
| 5,112,620 A | | 5/1992 | Repka et al. |
| 5,700,478 A | | 12/1997 | Biegajski et al. |
| 5,714,165 A | | 2/1998 | Repka et al. |
| 5,750,134 A | * | 5/1998 | Scholz et al. ............... 424/434 |
| 5,773,021 A | | 6/1998 | Gurtler et al. |
| 5,855,915 A | | 1/1999 | Pinkus |
| 5,955,097 A | | 9/1999 | Tapolsky et al. |
| 6,072,100 A | | 6/2000 | Mooney et al. |

OTHER PUBLICATIONS

Repka et al., "Influence of plasticizers and drugs on the physical–mechanical properties of hydroxypropylcellulose films prepared by hot melt extrusion", *Drug Dvlp. Ind. Pharm.* (1999), 25(5), 625–633.

McGinity et al., "Hot–melt extrusion technology", in *Encyclopedia of Pharmaceutical Technology* (Marcel Dekker, Inc., New York, NY, 2000).

* cited by examiner

Primary Examiner—Thurman K. Page
Assistant Examiner—Todd D Ware
(74) *Attorney, Agent, or Firm*—Rick Matos; Innovar, L.L.C.

(57) ABSTRACT

The present invention includes a hot-melt extruded film and method of preparation thereof. The film is made from a precursor composition containing at least a water soluble or water swellable thermoplastic polymer, preferably HPC and/or PEO, and a bioadhesive polymer. The film can also contain a therapeutic agent, preservative, buffering agent, antioxidant, super-disintegrant or absorbent, flavorant, colorant, water insoluble polymer, organic acid, surfactant, film modifier, and/or cross-linking agent. The film does not contain a conventional plasticizer or a material which is generally recognized in the art as a plasticizer for extruded films. The film can be sized and shaped to provide a controlled delivery of a therapeutic agent to the buccal, rectal, uterine, vaginal, abdominal, cranial, ophthalmic, nasal, sinus, or otic cavities. The film can also be used for the treatment of wounds.

36 Claims, 1 Drawing Sheet

FIG. 1

BIOADHESIVE HOT-MELT EXTRUDED FILM FOR TOPICAL AND MUCOSAL ADHESION APPLICATIONS AND DRUG DELIVERY AND PROCESS FOR PREPARATION THEREOF

CROSS-REFERENCE TO EARLIER FILED APPLICATIONS

The present application claims the benefit of priority of copending provisional application for patent Ser. No. 60/139,411 filed Jun, 16, 1999.

BACKGROUND OF THE INVENTION

Although a relatively new technology in the pharmaceutical industry, hot-melt extrusion has been used in the production of many different dosage forms and systems. It has been demonstrated to be applicable to various dosage forms including granules, pellets, and tablets. It has also been shown to provide numerous advantages in the production of thin films for both drug delivery and wound care applications. New chemical entities that face poor bioavailability due to solubility issues together with These drugs and pharmaceutical devices encompass not only prescription products but over-the-counter products (OTC) as well. Hot-melt extrusion technologies offer numerous advantages over traditional methods. Shorter and more efficient processing times to a final product, environmental advantages due to elimination of solvents in processing (including the possibility of recycling), and increased efficiency of drug delivery to the patient.

Thin films for transdermal/transmucosal (TD/TM) drug delivery devices and wound care applications are frequently produced via film casting utilizing organic or aqueous solvents. Aitken-Nichol, et al. (*Pharm. Res.*, 13:804–808 (1996); the entire disclosure of which is hereby incorporated by reference) noted numerous disadvantages accompanying these techniques including long processing times, high costs, and environmental concern. Gutierrez-Rocca, et al. (*DDIP.*, 19:315–332 (1993); the entire disclosure of which is hereby incorporated by reference) demonstrated that the attainment of stable mechanical properties might be as long as two months, which ultimately affects the rate of release of drugs incorporated into the films. In addition, moisture permeability and moisture uptake of TD/TM films may affect sustained drug release as well as adhesion of the films to the epidermis or mucosa. Hjartstam, et al. reported that alterations in cellulose film structure influenced both drug transport and the mechanical properties of the film. Also, levels and types of plasticizers, temperature, and relative humidity have been demonstrated to affect the physical-mechanical properties and the dissolution rate of drugs through films formed from aqueous dispersions.

Films comprising pure hydroxypropylcellulose (HPC) and other water-soluble or water-swellable polymers cannot be readily produced by hot-melt extrusion due to the high stress that is exhibited on the extruder. Therefore plasticizers have been added to the HPC and other polymers as described below.

U.S. Pat. No. RE 33,093 to Schiraldi et al. (the entire disclosure of which is hereby incorporated by reference) describes a bioadhesive hot-melt extruded film for intra-oral drug delivery and the processing thereof. The film of Schiraldi et al. comprises essentially a bioadhesive layer consisting of 40–95% by weight of a hydroxypropylcellulose (HPC), 5–60% of a homopolymer of ethylene oxide (PEO), 0–10% of a water-insoluble polymer, a medicament and 2–10% of a plasticizer. The film was made by a hot-melt extrusion process. Mooney, et al. (U.S. Pat. No. 6,072,100; the entire disclosure of which is hereby incorporated by reference) also describes a medicament delivery system consisting of HPC, PEO, a water-soluble polymer derived from acrylic acid, a medicament and a plasticizer. In this system, the compositions were intended for topical or transdermal delivery only. Note, however, that both of these references disclose that a plasticizer is needed for the production of a hot-melt extruded film.

It should be noted that there are numerous disadvantages to utilizing a plasticizer in hot-melt extruded films. Many plasticizers, such as those used by Mooney et al. are used are in liquid form, e.g., propylene glycol and glycerin. It is difficult to homogeneously disperse the plasticizer into a precursor composition prior to extrusion. Also, lower molecular weight plasticizers are unstable to high temperatures and may degrade or volatinize off during extrusion. Plasticizer stability is an issue as reported by Gutierrez-Rocca et al. and others. These plasticizers are generally very hygroscopic, which makes processing and packaging of films containing them problematic. This property of water absorption also may lead to drug degradation in that many drugs are susceptible to hydrolysis. Indeed, moisture in a hot-melt extruded film is extremely detrimental to the homogeneity and integrity of the film, in that film imperfections such as vacuoles from moisture evaporation during extrusion are incorporated. In general, a dry blend, without a plasticizer is extremely advantageous, eliminating or minimizing the problems discussed above.

Gurtler, et al. teaches the development of a bioadhesive ophthalmic insert. However, the ophthalmic insert requires the presences of a water-insoluble polymer. More importantly, however, the method of preparation and the thickness of the insert is different than the process and film claimed herein. The formation of a solid solution of the necessary medicament was carried out by Gurtler et al. using a solvent evaporation process. Also, when preparing an insert containing HPC and Carbopol 934P, the extrusion was carried out on a piston extruder requiring two successive extrusions to produce rods, 5 mm long (or thick) and 1.35 to 1.45 in diameter. Thus the thickness of the inserts is significantly greater than the thickness of the film claimed herein. Note that there was no need for Gurtler et al. to dry the ingredients used to form the inserts, since the inserts are rods and not films. In addition, when a solid solution of gentamycin was prepared by Gurtler et al. to form an ophthalmic insert, a three-step process was necessary, one of the steps of which included acetone evaporation. A solvent evaporation step is not included in the claimed process.

Accordingly, the prior art does not disclose that films comprising a major portion of HPC and other water-soluble or water-swellable polymers can be produced by hot-melt extrusion in the absence of a plasticizer. However, hot-melt extrusion possesses many processing advantages useful in the pharmaceutical industries. Therefore, a need remains for a bioadhesive hot-melt extruded film that does not contain a plasticizer.

SUMMARY OF THE INVENTION

The present invention provides a bioadhesive extruded film that is an effective, feasible, and convenient topical or intra-cavity drug delivery system for applying and delivering controlled dosages of therapeutic agents onto the skin or into the body cavities. This invention may also be extended to controlled drug delivery in skin care or cosmetics, gynecological, vaginal, cranial, abdominal, otic, uterine, nasal, sinus, rectal, buccal, oral, ophthalmlc, and wound care applications and to adhesive applications, such as for use as a denture adhesive. The present hot-melt extrusion process generally provides shorter and more efficient processing times to a final product, environmental advantages due to elimination of solvents in processing, better stability due to the elimination of a plasticizer, and increased efficiency of drug delivery to the patient.

It has now been discovered that HPC containing from about 1–25% polycarbophil (Noveon AA-1) may be hot-melt extruded in the absence of a conventional plasticizer to increase bioadhesion.

This invention is generally directed to an extruded single or multi-layered laminated relatively thin film (1 to 120 mils, or 25 to 3000 microns in thickness) that can be cut or formed into almost unlimited shapes and sizes, depending on the application intended. Films of different thickness are prepared by changing the extrusion die, varying the extrusion rate or varying the film tension between the chill-roll or take-off roll and the extruder. Thinner films are formed by using narrower gauge dies and/or by increasing the tension between the rolls and the extruder.

The film generally comprises one or more water-soluble or water-swellable thermoplastic polymers such as hydroxypropylcellulose, polyethylene oxide, homopolymers and copolymers of carboxymethyl cellulose, hydroxyethyl cellulose, hydroxymethyl cellulose) with a medicament in the absence of a plasticizer. The hot-melt extruded film may also comprise about 1 to 25 percent by weight of a water-soluble or water-swellable polymer derived from acrylic acid or a pharmaceutically acceptable salt thereof, such as the polyacrylic acid polymers as follows: Polycarbophil (Noveon AA-1), carbomer (Carbopol 974P or 971P or 907), or a water-soluble salt of a co-polymer of methyl vinyl ether and maleic acid or anhydride (Gantrez MS-955). The film can also comprise one or more pH adjusting compounds, additives, and/or hydrophobic polymers that may render the film useful for particular applications. The film is generally used for local treatment (oral ulcer), non-local treatment (dental caries, central acting anesthetic, i.e. delivery of drugs through the oral mucosa), or for bioadhesive applications only (such as a denture adhesive in which the system would not necessarily contain a medicament).

The film formulations of the invention will adhere to mucosal surfaces (oral, rectal, vaginal, etc.) and/or skin surfaces when wet.

Accordingly, one aspect of the invention provides a composition for forming a hot-melt extruded film, the composition comprising:

about 30–95% wt. of one or more water-soluble or water-swellable thermoplastic polymers;
about 1–25% wt., or up to 25% wt., of polycarbophil;
about 1–60% wt., or up to 60% wt., of poly(ethylene oxide);
about 0.1–10% wt., or up to 10% wt., of an organic acid;
about 0.01–10% wt., or up to 10% wt., of an antioxidant; and
about 0–50% wt., or up to 50% wt., of a therapeutic agent;
  wherein the composition can be hot-melt extruded into a film without extensive degradation in the absence of a conventional plasticizer.

Another aspect of the invention provides a hot-melt extruded film comprising:
about 50–99% wt., or up to 99% wt., of one or more water-soluble or water-swellable thermoplastic polymer or polymers;
about 0–50% wt., or up to 50% wt., of a therapeutic agent; and
about 1–25% wt., or up to 25% wt., polycarbophil; wherein the film has been hot-melt extruded without extensive degradation in the absence of a conventional plasticizer.

Still another aspect of the invention provides a hot-melt extruded film comprising:
about 50–99% wt., or up to 99% wt., of one or more water-soluble or water-swellable thermoplastic polymer or polymers;
about 0–50% wt., or up to 50% wt., of a therapeutic agent; and
about 1–25% wt., or up to 25% wt., of a bioadhesive polymer selected from the group consisting of polycarbophil, carbopol, GANTREZ® (which is a co-polymer of methyl vinyl ether and maleic acid or anhydride), one or more acrylic polymers, one or more polyacrylic acids, copolymers of these polymers, a water soluble salt of a co-polymer of methyl vinyl ether and maleic acid or anhydride (Gantrez MS-955), a combination thereof and their salts, wherein the film has been hot-melt extruded without extensive degradation in the absence of a conventional plasticizer.

The invention also provides a process for preparing a hot-melt extruded film comprising the steps of:

providing a precursor composition comprising about 50–99% wt. of one or more water soluble or water swellable polymers, about 0–50% wt., or up to 50% wt., of a therapeutic agent; and about 1–25% wt., or up to 25% wt., of a bioadhesive polymer; and hot-melt extruding the precursor composition to form a film;

wherein the precursor composition is hot-melt extruded without extensive degradation in the absence of a plasticizer.

Preferred embodiments of the invention include those wherein: 1) the film comprises a therapeutic agent; 2) the film is a denture adhesive when wetted with an aqueous solution or oral fluids; 3) the film is adapted for controlled delivery of a therapeutic agent to the buccal, oral, rectal, vaginal, abdominal, cranial, ophthalmic or otic cavities; 4) the extruded film is granulated and/or pulverized for use as a powder type adhesive; 5) the film comprises one or more pH adjusting agents; 6) the hot-melt extruded thin film is cut to a specific size and/or shape, especially prior to use as a denture adhesive; 7) the film comprises one or more film modifiers; 8) the film comprises a single layer; 9) the film comprises two or more layers; 10) the film comprises a super-disintegrant or super-absorbent; 11) the film contains a polyacrylic acid; 12) the film contains a water-insoluble polymer; 13) the composition, film and/or one or more thermoplastic polymers contain less than 2% wt. water, more preferably less than 1% wt. water, or most preferably less than 0.5% wt. water; 14) the film is about 1–120 mils, or about 25–3000 microns, thick; 15) the film includes one or more water insoluble polymers; 16) a buffering agent is present in an amount ranging from about 0.1–7.5% wt. or up to about 7.5% wt.; and/or 17) a preservative is present in an amount ranging from about 0.01–0.5% wt., about 0.02–0.2% wt., or up to about 0.5% wt.

BRIEF DESCRIPTION OF THE FIGURE

The following drawing is part of the present specification and is included to further demonstrate certain aspects of the invention. The invention may be better understood by reference to this drawing in combination with the detailed description of the specific embodiments presented herein.

DETAILED DESCRIPTION OF THE INVENTION

The present invention provides a precursor composition for forming a bioadhesive thin film by hot-melt extrusion and the thin film so formed. The film is useful for delivering one or more drugs through the skin or mucosal tissue. The film generally comprises water-soluble or water-swellable thermoplastic polymers, such as hydroxypropylcellulose (HPC) and polyethylene oxide (PEO) and a medicament. Also, polycarbophil, carbopol, GANTREZ®, or other acrylic polymers or polyacrylic acids or copolymers of these polymers and their salts may be present in the extruded film. The film can be used as a denture adhesive (with or without medicament) that has a bioadhesive quality when the film is wetted.

The hot-melt extruded, bioadhesive film of the present invention generally comprises a hydroxyalkylcellulose, such as hydroxypropylcellulose, a medicament and from about 1 to 25 percent of an acrylic acid polymer such as polycarbophil (Noveon AA-1) or carbomer (Carbopol 974P or 971P) or a water soluble salt of a co-polymer of methyl vinyl ether and maleic acid or anhydride (Gantrez MS-955), or a combination thereof.

The HPC or other water-soluble or water-swellable thermoplastic polymer or polymers are generally present in the film and precursor composition in amounts ranging from about 50–99% wt. of the film.

The HPC is available from commercial suppliers including, for example, Aqualon, Inc., (Wilmington, DE). The HPC generally has an average molecular weight in the range of about 60,000 to 1,200,000. The preferred HPC or other water-soluble or water-swellable polymer(s) will generally have the following properties: Thermoplastic, with desirable extrudable properties and stability.

Other water soluble or water swellable thermoplastic polymers include poly(ethylene oxide). The film comprises one or more thermoplastic polymers; therefore, it can include HPC in combination with PEO, for example.

The water insoluble polymer(s) that can be contained within the film include, by way of example and without limitation, alkylcelluloses, ethylcellulose, methylcellulose, and others known to those of ordinary skill in the art.

The hot-melt extruded film can also comprise one or more pH-adjusting agents to improve drug stability and solubility. Also the pH modifying agents can control drug release and enhance bioadhesion. These additives may be dispersed in the powder blend, and the pH adjusted from 2.0 to 10.0, or more optimally from 4.0 to 8.5. The pH-adjusting agent is generally present in an amount of about 0.1–10% wt., while 2–6% is most desirable. A pH-adjusting agent can include, by way of example and without limitation, an organic acid or base, an alpha-hydroxy acid, a beta-hydroxy acid. Suitable agents include tartaric acid, citric acid, fumaric acid, succinic acid and others known to those of ordinary skill in the art.

The hot-melt extruded film can also comprise one or more cross-linking agents to reduce matrix erosion time, control drug release, or enhance bioadhesion. A cross-linking agent is defined as any compound that will form cross-links between the hydroxyl moieties of the HPC. A cross-linking agent can include, by way of example and without limitation, an organic acid, an alpha-hydroxy acid, a beta-hydroxy acid. Suitable cross-linking agents include tartaric acid, citric acid, fumaric acid, succinic acid and others known to those of ordinary skill in the art. The cross-linking agents, in particular the alpha-hydroxy acids and beta-hydroxy acids, may be used for medicinal and/or cosmetic purposes. When present, the cross-linking agent will be present in an amount ranging from about 0.1–15% wt. based upon the weight of the film.

The extruded film may also contain up to about 20 percent by weight, based upon the weight of the film, of other components that modify the extrusion characteristics or physical properties of the film. Such other components are well known to those of ordinary skill in the pharmaceutical sciences and include, for example, polyethylene, ethyl cellulose, polyvinylpyrrolidone, (Kollidon), polyethylene oxide (PolyOx), xylitol, sucrose, surface-active agents, others known to those skilled in the art, and combinations thereof.

The film of the present invention can also include super-disintegrants, or in this case absorbents. The presence of these absorbents make the film more rigid without the use of a plasticizer, however, it becomes more flexible when in contact with moisture on the skin or on mucosal membranes. Examples of such are sodium starch glycolate (Explotab™, Primojel™) and croscarmellose sodium (Ac-Di-Sol®), which we have discovered effectively enhance the moisture absorbing capacity of the film, a property which is particularly desirable for wound care applications. Other suitable absorbents include cross-linked PVP (Polyplasdone™ XL 10), veegum, clays, alginates, PVP, alginic acid, carboxymethylcellulose calcium, microcrystalline cellulose (e.g., Avicel™), polacrillin potassiium (e.g., Amberlite™), sodium alginate, corn starch, potato starch, pregelatinized starch, modified starch, cellulosic agents, montmorrilonite clays (e.g., bentonite), gums, agar, locust bean gum, gum karaya, pecitin, tragacanth, and other disintegrants known in to those of ordinary skill in the art. When present, the super-disintegrant (or absorbents) will be present in the range of about 0.1–20% wt. based upon the weight of the film. Some of these materials are also considered water soluble thermoplastic or non-thermoplastic polymers.

The bioadhesive film of the present invention is particularly useful in topical or intra-orally adhesive applications, or for controlled release delivery of a drug or medicament to skin or mucosa. Accordingly, the film includes 0 to about 50% wt. of one or more medicaments that can be administered through the skin or mucosa. Such medicaments include, for example, analgesics, anesthetics, anti-inflammatory agents, antihistamines, decongestants, antibiotics, anti-caries agents, antibacterials, antifungals, anti-acne agents, antiseptics, chemotherapeutic agents, vitamins, minerals, hormones, proteins, peptides, enzymes, others known to those of ordinary skill in the medical arts, and combinations thereof. The therapeutic agents are included in therapeutically effective amounts in the film or segments thereof.

Also, some medicaments are not stable under the temperature and shearing conditions of the hot-melt extrusion process. However, these can be applied to the extruded films using techniques that are known to those skilled in the art. For example, these medicaments can be dissolved in a solvent and coated onto the extruded films.

The bioadhesive film can also include one or more of each of a pH buffering agent, an antioxidant, chelating agent, stabilizer, surfactant, preservative, paraben, flavor, colorant, fragrance and combinations thereof.

PH buffering agents include alkalinizing agents, acidifying agents and salts thereof. Buffering agents are used to control the pH of an aqueous solution in which the film is immersed. A buffering agent is used to resist change in pH upon dilution or addition of acid or alkali. Such compounds include, by way of example and without limitation, potassium metaphosphate, potassium phosphate, monobasic sodium acetate and sodium citrate anhydrous and dihydrate, salts of inorganic or organic acids, salts of inorganic or organic bases, and others known to those of ordinary skill in the art.

As used herein, the term "acidifying agent" is intended to mean a compound used to provide acidic medium for product stability. Such compounds include, by way of example and without limitation, acetic acid, amino acid, citric acid, fumaric acid and other alpha hydroxy acids, such as hydrochloric acid, ascorbic acid, nitric acid and others known to those of ordinary skill in the art.

As used herein, the term "alkalinizing agent" is intended to mean a compound used to provide alkaline medium for product stability. Such compounds include, by way of example and without limitation, ammonia solution, ammonium carbonate, diethanolamine, monoethanolamine, potassium hydroxide, sodium borate, sodium carbonate, sodium bicarbonate, sodium hydroxide, triethanolamine, and trolamine and others known to those of ordinary skill in the art.

The film and precursor composition of the invention can include a chelating agent. Suitable chelating agents include EDTA, polycarboxylic acids, polyamines, derivatives thereof, and others known to those of ordinary skill in the art.

The film and precursor composition of the invention can include a surfactant. Suitable surfactants include sucrose stearate, Vitamin E derivatives, sodium lauryl sulfate, dioctyl sodium sulfosuccinate, and others known to those of ordinary skill in the art.

The film and precursor composition of the invention can include a preservative. Preservatives include compounds used to prevent the growth of microorganisms. Suitable preservatives include, by way of example and without limitation, benzalkonium chloride, propyl paraben, methyl paraben, benzethonium chloride, benzyl alcohol, cetylpyridinium chloride, chlorobutanol, sorbic acid, phenol, phenylethyl alcohol, phenylmercuric nitrate and thimerosal and others known to those of ordinary skill in the art.

As used herein, the term "flavorant", "flavor" or "fragrance" is intended to mean a compound used to impart a pleasant flavor and often odor to a pharmaceutical preparation. In addition to the natural flavorants, many synthetic flavorants are also used. Such compounds include, by way of example and without limitation, anise oil, cinnamon oil, cocoa, menthol, orange oil, peppermint oil and vanillin and others known to those of ordinary skill in the art. Flavors incorporated in the composition may be chosen from synthetic flavor oils and flavoring aromatics and/or natural oils, extract from plants, leaves, flowers, fruits and so forth and combinations thereof. These may include oil of wintergreen, clove oil, bay oil, anise oil, eucalyptus, thyme oil, cedar leaf oil, oil of nutmeg, oil of sage, oil of bitter almonds and cassia oil. Also useful as flavors are vanilla, citrus oil, including lemon, orange, grape, lime and grapefruit, and fruit essences, including apple, pear, peach, strawberry, raspberry, cherry, plum, pie, apricot, and so forth. Flavors that have been found to be particularly useful include commercially available orange, grape, cherry, and bubble gum flavors and mixtures thereof. The amount of flavoring may depend on a number of factors, including the organoleptic effect desired.

As used herein, the term "colorant" is intended to mean a compound used to impart color to solid pharmaceutical preparations. Such compounds include, by way of example and without limitation, FD&C Red No. 3, FD&C Red No. 20, FD&C Yellow No. 6, FD&C Blue No. 2, D&C Green No. 5, D&C Orange No. 5, D&C Red No. 8, caramel, and ferric oxide red. Other suitable colorants include titanium dioxide and natural coloring agents such as grape skin extract, beet red powder, beta-carotene, annato, carmine, turmeric, paprika, and others known to those of ordinary skill in the art.

As used herein, the term "antioxidant" is intended to mean an agent that inhibits oxidation and thus is used to prevent the deterioration of preparations by oxidation. These compounds have been discovered to be essential when using some of the water-soluble or water-swellable polymers, such as PEO. These compounds include, by way of example and without limitation, ascorbic acid, ascorbyl palmitate, butylated hydroxyanisole, butylated hydroxytoluene, hypophosphorous acid, monothioglycerol, sodium ascorbate, sodium formaldehyde sulfoxylate and sodium metabisulfite and others known to those of ordinary skill in the art. Other suitable antioxidants include, for example, vitamin C, BHT, BHA, sodium bisulfite, vitamin E and its derivatives, propyl gallate, a sulfite derivative, and others known to those of ordinary skill in the art.

Embodiments of the film that provide a controlled release of an agent may contain a release rate modifier. Suitable release rate modifiers include hydroxypropylcellulose (HPC), poly(ethylene oxide) (PEO), hydroxypropyl methylcellulose (HPMC), ethylcellulose, cellulosic polymers, acrylic polymers, fat, waxes, lipid, or a combination thereof. In some embodiments, the release rate modifier is polycarbophil, carbomer or a polysaccharide.

Figure 1:
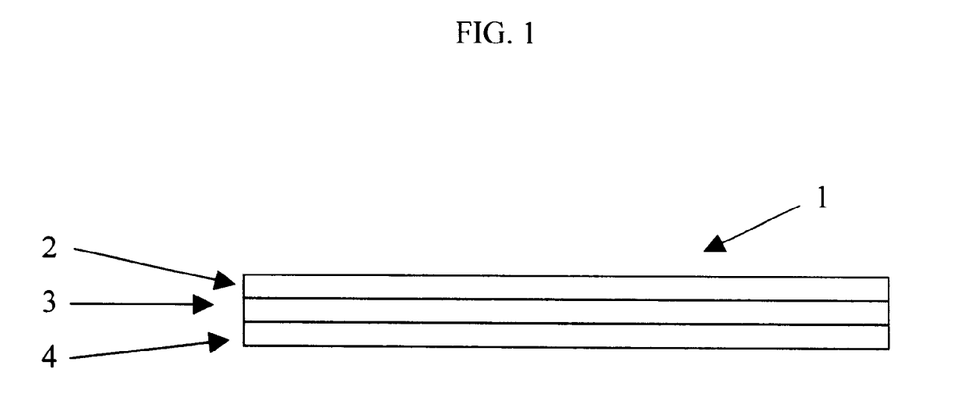
FIG. 1 depicts a side-view of a multi-layered bioadhesive hot-melt extruded film prepared according to the invention.

The film of the present invention comprises at least one bioadhesive extruded film layer. It may also further comprise a therapeutic agent reservoir layer and/or an outer protective barrier membrane layer. FIG. 1 depicts a multi-layered film (1) according to the invention comprising an outer protective barrier or backing layer (2), a reservoir or drug-matrix layer (3) and an adhesive layer (4). If for medicinal purposes, the therapeutic agent may be incorporated into any or all of the layers. In some cases the single or multi-layer system may require a suitable adhesive layer (silicones, etc).

When the film is used in conjunction with or as a bandage or wound dressing, the multi-layered film can comprise conventional adhesive or non-adhesive bandages or wound dressings of the medical or surgical type. Generally such bandages include a plastic film backing having attached thereto an absorbent pad portion. The absorbent pad material may be any of the woven or non-woven fabrics of natural or synthetic fibers heretofore employed as dressings, including for example, cotton, nylon or polyester. Suitable substrates further include woven or standard papers, and plastics. Preferred Ad substrates include absorbent pad materials comprised of a rayon and polypropylene (10:90 weight ratio) spun bonded web, a knitted polyester fabric such as that used for DERMICEL taffeta tape manufactured by Johnson & Johnson Consumer Products, Inc., Skilhman, N.J., and a composite nonwoven fabric made of thin, breathable polyester/polyurethane laminate known as FABRELLE which is manufactured by Fabrite Industries, Woodbridge, N.J.

Suitable plastic film backings include highly plasticized polyvinyl chloride, polyurethane, polyolefins, ethylene vinyl acetate and block copolymers films such as HYTREL® copolyester ether elastomers available from E. I. DuPont, Wilmington, Del. These plastic films may or may not contain an adhesive, which may or may not be pressure sensitive.

Adhesive bandages can also include one or more release tabs. Release tabs (such as silicone-coated release paper or other alternate materials which can be readily removed at the time of use), are applied so as to cover, in an overlaying manner, the entire adhesive side of an adhesive bandage.

In addition, each bandage can be packaged and sealed in an individual wrapper (which typically is made of glassine-paper or a similar bacterial barrier material). Each bandage is packaged before it undergoes ethylene oxide or irradiation sterilization so as to maintain sterility until the bandage is ready for use.

In the case of a multi-layered film comprising at least two layers, the different layers may be co-extruded and then laminated onto each other, or extruded separately and then laminated onto each other. Lamination of the layers is conducting using any conventional method known to those of skill in the polymer film arts. Such methods include, for example, co-extrusion. An adhesive layer may also be laminated onto the adhesive-matrix if necessary. Again, this layer may be added in a co-extrusion process or laminated after extrusion. Also, an outer backing, protective membrane layer may be part of the system.

By varying the ratio of additive polymers, such as polysaccharides, hydrophobic polymers (ethyl cellulose, acrylates, etc.) or other hydrophilic polymers, including polyethylene oxide and cellulose derivatives, one may control the solubility and the erosion of the film and the bioadhesive properties of the film to the skin or mucous membranes.

The temperature required to extrude the film is dependent upon on the properties of the components that comprise the precursor composition used to form film. The precursor compositions are extruded at their respective optimal temperatures, which usually is from 100° C. to 200° C. However, temperatures may vary from 60° C. to 250° C. The optimal temperature for extrusion is determined by the thermal stability of the active ingredient and the composition of the film.

The particle size of the components present in the precursor composition may affect the properties and characteristics of the extruded film and the processability of the precursor composition. Optimal particle size is determined depending on the physical properties of the compounds and the processing conditions that the materials will be subjected.

The moisture content of the components present in the precursor composition may affect the properties and characteristics of the extruded film and the processability of the precursor composition. If excessive moisture is present in the extruded film, volatilization of the water will result in vacuoles and other imperfections within the film. Unlike extruded rods and other hot-melt extruded shapes, films are extremely sensitive to moisture content. It may be necessary to dry the ingredients before and after mixing in order to keep moisture content to a minimum or to below an acceptable level. For film production in most cases, the preferred moisture content is less than 2% wt., more preferably less than 1% wt. or less than 5% wt.

In order to minimize degradation of the components of the precursor composition or of the film, the residence time of the components in the hot-melt extruder is generally kept to a minimum. The optimal residence time is generally less than about 120 seconds, and preferably less than about 30 seconds.

The hot-melt extruded film of the invention is of acceptable quality, preferably pharmaceutically acceptable quality. The film, after extrusion, is generally free of pock-marks, holes, fissures, cracks, breaks and other undesired features typically associated with hot-melt extruded films that are extruded in the absence of a plasticizer.

The foregoing will be better understood with reference to the following examples that detail certain procedures for the preparation of formulations according to the present invention. All references made to these examples are for the purposes of illustration. They are not to be considered limiting as to the scope and nature of the present invention.

The following examples are included to demonstrate preferred embodiments of the invention. It should be appreciated by those of skill in the art that the techniques disclosed in the examples which follow represent techniques discovered by the inventors to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

EXAMPLE 1

This example describes a monolayer denture adhesive film (15 mils thick) and method of preparation therefor. No medicament is necessary for this film.

| Ingredients | Amounts (% wt.) |
|---|---|
| Hydroxypropylcellulose (Klucel-HF, Aqualon Company) | 88.78 |
| Polycarbophil (Noveon AA-1, BF Goodrich) | 8.00 |
| Tartaric Acid | 3.00 |
| Methyl paraben | 0.20 |
| Propyl paraben | 0.02 |

All of the above ingredients were processed to obtain the appropriate particle size. In the case of polycarbophil and carbomer, a 20-mesh screen was utilized. The tartaric acid was sieved through a <80-mesh screen to attain optimal particle size. The methyl paraben and propyl paraben were also sieved through a <100-mesh screen. Each of the ingredients was oven dried prior to use. The polycarbophil, the carbomer, and the super-disintegrants, such as the sodium starch glycolate (Example 3) were oven dried for at least 48 hours at 50° C. The ingredients were mixed in a powder blender for a period of about 20 minutes. After adequate blending, the powder blend was dried again for about 24 hours at 50° C. After the extruder had been pre-heated and pre-set to the appropriate rpm (100 rpm in this case), the dried blend was removed from the oven and directly added to the hopper of the extruder. The extrusion process was carried out in a controlled environment (22–27° C., <30% RH). The extrusion was conducted with a suitable extruder (e.g. Killion model KLB-125) with adequate downstream equipment (chill-roll and take-off roller). The extrusion temperature profile used for the different sections of the screw is listed below.

| Zone (Barrel or Die) | Temperature (° C.) |
|---|---|
| Zone 1 | 150 |
| Zone 2 | 155 |
| Zone 3 | 160 |
| Zone 4 | 170 |
| Zone 5 | 175 |
| Zone 6 | 180 |
| Die Zone | 190 |

The films were extruded at a rate of about approximately 15 feet per minute using a 6-inch flex-lip die. The final film width was about 5 ½ inches. If desired the film may then be granulated or pulverized with appropriate equipment to provide an adhesion system other than the extruded film itself.

EXAMPLE 2

This example describes a monolayer denture adhesive film (15 mils thick) and method of preparation therefor. This film was made according to the process of Example 1 except that no tartaric acid was used.

| Ingredients | Amounts (% wt.) |
|---|---|
| Hydroxypropylcellulose (Klucel-HF, Aqualon Company) | 91.78 |
| Polycarbophil (Noveon AA-1, BF Goodrich) | 8.00 |
| Methyl paraben | 0.20 |
| Propyl paraben | 0.02 |

EXAMPLE 3

This example describes a monolayer denture adhesive film (15 mils thick) and method of preparation therefor. This film is made according to the process of Example 1. The film is die-cut into a denture shape or cut into strips for application to the denture.

| Ingredients | Amounts (% wt.) |
|---|---|
| Hydroxypropylcellulose (Klucel-HF, Aqualon Company) | 67.70 |
| Polyethylene Oxide (PolyOx, Union Carbide) | 30.00 |
| BHT | 0.10 |
| Ascorbic Acid | 2.00 |
| Methyl paraben | 0.20 |

EXAMPLE 4

This example describes a monolayer topical wound care patch adhesive film (10–15 mils thick) and method of preparation therefor. This film was made according to the process of Example 1 except that no tartaric acid was used. The film was cut into various bandage sizes for the appropriate application. The film may contain an adhesive layer overlaying and extending ⅛ to 2 inches beyond the patch. It is extremely useful in wound exudate absorption.

| Ingredients | Amounts (% wt.) |
|---|---|
| Hydroxypropylcellulose (Klucel-HF, Aqualon Company) | 79.78 |
| Polyvinylpyrrolidone (Kollidon) | 5.00 |
| Polycarbophil (Noveon AA-1) | 5.00 |
| Sodium starch glycolate (Explotab, Mendell) | 8.00 |
| Carbomer (Carbopol 971P, BF Goodrich) | 3.00 |
| Methyl paraben | 0.20 |
| Propyl paraben | 0.02 |

EXAMPLE 5

The following example is another illustration of a single layer topical wound care patch that may be cut into various bandage sizes for the appropriate application. Note that it has a higher percent of super-disintegrant (absorbent). It is useful when more exudate absorption is needed. This film was made according to the process of Example 1.

| Ingredients | Amounts (% wt.) |
|---|---|
| Hydroxypropylcellulose (Klucel-HF, Aqualon Company) | 73.78 |
| Polycarbophil (Noveon AA-1, BF Goodrich) | 8.00 |
| Carbomer (Carbopol 971P, BF Goodrich) | 2.00 |
| Sodium starch glycolate (Explotab, Mendell) | 16.00 |
| Methyl paraben | 0.20 |
| Propyl paraben | 0.02 |

EXAMPLE 6

This example provides an intra-oral, single-layer film containing triamcinolone acetonide as an anti-inflammatory agent and lidocaine as a local anesthetic for local application to an ulcer on the oral mucosa. This film was made according to the process of Example 1.

| Ingredients | Amounts (% wt.) |
|---|---|
| Hydroxypropylcellulose (Klucel-HF, Aqualon Company) | 80.58 |
| Polycarbophil (Noveon AA-1, BF Goodrich) | 4.00 |
| Ascorbic Acid | 2.00 |
| Polyethylene Oxide (PolyOx, Union Carbide) | 7.00 |
| Tartaric Acid | 4.00 |
| Methyl paraben | 0.20 |
| Propyl paraben | 0.02 |
| Lidocaine (Spectrum Chemicals) | 2.00 |
| Triamcinolone acetonide (Upjohn) | 0.10 |

EXAMPLE 7

The following formulation for an extruded film (7 mils thick) is useful as a topical, cosmetic (face or hand) mask or patch for wrinkles and aging spots. This film is made according to the process of Example 1.

| Ingredients | Bioadhesive matrix (%) |
|---|---|
| Hydroxypropylcellulose (Klucel-JF) | 69.90 |
| Polycarbophil (Noveon AA-1) | 3.00 |

-continued

| Ingredients | Bioadhesive matrix (%) |
|---|---|
| Gantrez MS-955 | 3.00 |
| Tartaric Acid | 1.00 |
| Citric Acid | 1.00 |
| Polyethylene oxide (PolyOx) | 20.00 |

| | |
|---|---|
| Vitamin E | 0.50 |
| Glycerides (Miglyol 812) | 1.00 |
| BHT | 0.10 |
| Methyl paraben | 0.20 |
| Propyl paraben | 0.02 |

EXAMPLE 8

The following is a topical anti-inflammatory patch for localized rashes, insect bites, etc. The film may be cut and shaped into appropriately sized sections as needed. A protective backing may or may not be utilized. This film was made according to the process of Example 1.

| Ingredients | Bioadhesive matrix (%) [7 mils] |
|---|---|
| Hydroxypropylcellulose (Klucel-HF) | 70.68 |
| Carbomer (Carbopol 974P) | 5.00 |
| Eudragit E-100 | 5.00 |
| Polyethylene Oxide (PolyOx) | 12.00 |
| Polyethylene | 4.00 |
| Ascorbic Acid | 2.00 |
| BHT | 0.10 |
| Methyl paraben | 0.20 |
| Propyl paraben | 0.02 |
| Hydrocortisone | 1.00 |

EXAMPLE 9

This formulation is extruded and shaped such that the film may be inserted rectally with an appropriate applicator to treat hemorrhoid discomfort.

| Ingredients | Bioadhesive matrix (%) [8 mils] |
|---|---|
| Hydroxypropylcellulose (Klucel-MF) | 83.90 |
| Gantrez MS-955 | 6.00 |
| BHT | 0.10 |
| Benzocaine | 10.00 |

EXAMPLE 10

This film formulation was made according to Example 9 except that the benzocaine was replaced with an anti-fungal agent such as miconazole, and the Gantrez was replaced with polycarbophil. This film can be used for vaginal fungal infections and can be inserted with or without an appropriate applicator into the vaginal cavity.

EXAMPLE 11

This formulation may be utilized as a two or three layer anesthetic film for intra-oral use.

| Ingredients | Inner matrix (%) | Outer backing layer |
|---|---|---|
| Hydroxypropylcellulose (Klucel-MF) | 80.90 | 60.00 |
| Polycarbophil (Noveon AA-1) | 6.00 | |
| Gantrez MS-955 | 1.00 | |
| Polyethylene | 4.00 | |
| Ethyl cellulose | 1.00 | 37.00 |
| BHT | 0.10 | |
| Benzocaine | 7.00 | |
| Eudragit E-100 | | 2.00 |
| Polyethylene glycol 3350 | | 1.00 |

In this case, the films is co-extruded and lamination is attained immediately after each individual film is extruded on two Killion extruders.

EXAMPLE 12

The following tri-layer film is utilized in treating intra-oral lesions such as aphthous ulcers. These may be co-extruded and laminated or laminated after extrusion.

| Ingredients | Inner matrix (%) | Medicated layer | Outer backing layer |
|---|---|---|---|
| Hydroxypropylcellulose (Klucel-MF) | 87.00 | 72.80 | 58.00 |
| Carbomer (Carbopol 974P) | 4.00 | | |
| Gantrez MS-955 | 4.00 | | |
| Polyethylene | 5.00 | | |
| Ethyl cellulose | | 20.00 | 41.00 |
| BHT | | 0.10 | |
| Benzocaine | | 5.00 | |
| Triamcinolone acetonide | | 0.10 | |
| Glycerides (Miglyol 812) | | 2.00 | 1.00 |

The values expressed as weight percentages herein are generally based upon the total weight of the film or the precursor composition.

The above is a detailed description of particular embodiments of the invention. It is recognized that departures from the disclosed embodiments may be made within the scope of the invention and that obvious modifications will occur to a person skilled in the art. Those of skill in the art should, in light of the present disclosure, appreciate that many changes can be made in the specific embodiments which are disclosed herein and still obtain a like or similar result without departing from the spirit and scope of the invention. All of the embodiments disclosed and claimed herein can be made and executed without undue experimentation in light of the present disclosure.

We claim:

1. A hot-melt extruded composition comprising:
   about 30–95% wt. of one or more water-soluble or water-swellable thermoplastic polymers;
   about 1–25% wt. of polycarbophil;
   about 1–60% wt. of poly(ethylene oxide);
   about 0.1–10% wt. of an organic acid;
   about 0.01–10% wt. of an antioxidant; and
   about 0–50% wt. of a therapeutic agent; wherein the composition has been hot-melt extruded without extensive degradation in the absence of a plasticizer.

2. The composition according to claim 1 further comprising a buffering agent present in an amount of about 0.1–10.0% wt.

3. The composition according to claim 1 further comprising a preservative present in an amount of about 0.01–0.5% wt.

4. The composition according to claim 1 further comprising about 0.1–20% wt. of a super-disintegrant or absorbent.

5. The composition according to claim 4, wherein the super-disintegrant or absorbent is selected from the group consisting of sodium starch glycolate, croscarmellose sodium, cross-linked PVP, veegum, clay, alginate, PVP, alginic acid, carboxymethylcellulose calcium, microcrystalline cellulose, polacrillin potassium, sodium alginate, corn starch, potato starch, pregelatinized starch, modified starch, cellulosic agent, gum, agar, pectin, and tragacanth.

6. The composition of claim 2, wherein the buffering agent is selected from the group consisting of potassium metaphosphate, potassium phosphate, monobasic sodium acetate and sodium citrate anhydrous and dihydrate, salt of an inorganic acid, salt of an organic acid, salt of an inorganic base, and salt of an organic base.

7. The composition of claim 1, wherein the therapeutic agent is selected from the group consisting of analgesics, anesthetics, anti-inflammatory agents, antihistamines, decongestants, antibiotics, anti-caries agents, antibacterials, antifungals, anti-acne agents, antiseptics, chemotherapeutic agents, vitamins, minerals, hormones, proteins, peptides, enzymes, and combinations thereof.

8. The composition of claim 1, wherein the antioxidant is selected from the group consisting of ascorbic acid, ascorbyl palmitate, butylated hydroxyanisole, butylated hydroxytoluene, hypophophorous acid, monothioglycerol, sodium ascorbate, sodium formaldehyde sulfoxylate, sodium metabisulfite, vitamin C, BHT, BHA, sodium bisulfite, vitamin E and its derivatives, propyl gallate, and a sulfite derivative.

9. The composition of claim 1, wherein the thermoplastic polymer is HPC.

10. The composition of claim 1 further comprising up to about 20% wt. of a material selected from the group consisting of polyethylene, ethyl cellulose, polyvinylpyrrolidone, xylitol, sucrose, a surface-active agent, and a combination thereof.

11. A hot-melt extruded film comprising:
    about 50–99% wt. of one or more water-soluble or water-swellable thermoplastic polymer or polymers;
    about 0–50% wt. of a therapeutic agent; and
    about 1–25% polycarbophil; wherein the film has been hot-melt extruded without extensive degradation in the absence of a plasticizer.

12. A hot-melt extruded film comprising:
    about 50–99% wt. of one or more water-soluble or water-swellable thermoplastic polymer or polymers;
    about 0–50% wt. of a therapeutic agent; and
    about 1–25% wt. of a bioadhesive polymer selected from the group consisting of polycarbophil, carbopol, a co-polymer of methyl vinyl ether and maleic acid or anhydride, one or more acrylic polymers, one or more polyacrylic acids, copolymers of these polymers, a water soluble salt of a co-polymer of methyl vinyl ether and maleic acid or anhydride, a combination thereof and their salts, wherein the film has been hot-melt extruded without extensive degradation in the absence of a plasticizer.

13. A hot-melt extruded film according to claim 11 or 12 wherein the film is a denture adhesive when wetted with an aqueous solution or oral fluids.

14. A hot-melt extruded film according to claim 11 or 12, wherein a therapeutic agent is present, and the film is adapted for controlled delivery of the therapeutic agent to the buccal, oral, rectal, vaginal, abdominal, cranial, ophthalmic or otic cavity.

15. A powdered adhesive comprising a granulated and/or pulverized hot-melt extruded film according to claim 11 or 12.

16. A hot-melt extruded film according to claim 11 or 12, wherein the film further comprises one or more cross-linking agents present in an amount of about 0.1–15% wt.

17. A hot-melt extruded film according to claim 11 or 12, wherein the film further comprises one or more film modifiers present in an amount of up to about 20% wt.

18. A hot-melt extruded film according to claim 11 or 12, wherein the film further comprises two or more layers.

19. A hot-melt extruded film according to claim 11 or 12, wherein the film further comprises a super-disintegrant or super-absorbent present in an amount of about 0.1–20% wt.

20. A hot-melt extruded film according to claim 11 or 12, wherein the film further comprises a ph-modifiing agent present in an amount of about 0.1–10.0% wt.

21. A hot-melt extruded film according to claim 11 or 12, wherein the film further comprises a preservative present in an amount of about 0.01–0.5% wt.

22. A hot-melt extruded film according to claim 11 or 12, wherein the film further comprises an organic acid present in an amount of about 0.1–10% wt.

23. A hot-melt extruded film according to claim 11 or 12, wherein the film further comprises a water insoluble polymer present in an amount of about 1.0 to 20%.

24. A process for preparing a hot-melt extruded film comprising the steps of:
    providing a precursor composition comprising about 50–99% wt. of one or more water-soluble or water-swellable thermoplastic polymers; about 0–50% wt of a therapeutic agent; and about 1–25% wt. of a bioadhesive polymer; and
    hot-melt extruding the precursor composition in the absence of a plasticizer to form a first film.

25. The process of claim 24 further comprising the step of drying the precursor composition or its components prior to hot-melt extruding the composition.

26. The process of claim 25, wherein the moisture content of the precursor composition is less than about 2% wt. after drying.

27. The process of claim 24, wherein the precursor composition comprises a therapeutic agent.

28. The process of claim 24, wherein the hot-melt extruding step forms a first film having a thickness in the range of about 1–120 mils.

29. The process of claim 24, wherein the thermoplastic polymer is selected from the group consisting of HPC, PEO and a combination of HPC and PEO.

30. The process of claim 29, wherein the bioadhesive polymer is selected from the group consisting of polycarbophil, carbomer, one or more acrylic polymers, one or more polyacrylic acids, copolymers of these polymers, a water soluble salt of a co-polymer of methyl vinyl ether and maleic acid or anhydride, a combination thereof and their salts.

31. The process of claim 30, wherein the precursor composition further comprises one or more of the following additional components:
    a) one or more film modifiers present in an amount of up to about 20% wt.;
    b) one or more cross-linking agents present in an amount of about 0.1–1 5% wt.;
    c) a super-disintegrant or super-absorbent present in an amount of about 0.1–20% wt.;

d) a pH-modifying agent present in an amount of about 0.1–10.0% wt.;

e) a preservative present in an amount of about 0.01–0.5% wt.;

f) an organic acid present in an amount of about 0.1–10% wt.; and g) a water insoluble polymer present in an amount of about 1.0–20%.

32. The process of claim 31 wherein the precursor composition comprises at least two additional components.

33. The process of claim 24 further comprising the steps of extruding a second composition to form a second film and laminating the first and second films.

34. The process of claim 24 further comprising the step of cutting or shaping the film to adapt it for delivery of the therapeutic agent to the buccal, oral, rectal, vaginal, abdominal, cranial, ophthalmic, uterine, nasal, sinus or otic cavity.

35. A hot-melt extruded film according to claim 11 or 12, wherein the film is comprised in a bandage or wound dressing.

36. The composition according to any one of claims 1–10, wherein the composition is a film.

* * * * *